US005893839A

United States Patent [19]
Johnson

[11] Patent Number: 5,893,839
[45] Date of Patent: Apr. 13, 1999

[54] TIMED-RELEASE LOCALIZED DRUG DELIVERY BY PERCUTANEOUS ADMINISTRATION

[75] Inventor: Matthew S. Johnson, Carmel, Ind.

[73] Assignee: Advanced Research And Technology Institute, Inc., Bloomington, Ind.

[21] Appl. No.: 08/816,670

[22] Filed: Mar. 13, 1997

[51] Int. Cl.$^6$ .................................................. A61M 31/00
[52] U.S. Cl. .......................... 604/51; 604/57; 604/49; 424/424
[58] Field of Search .................... 604/51, 57, 158, 604/159, 160, 164, 165, 166, 170, 48, 49, 59, 60, 73; 606/170; 424/424; 623/1

[56] References Cited

U.S. PATENT DOCUMENTS

| | | | |
|---|---|---|---|
| 4,898,734 | 2/1990 | Mathiowitz et al. | 424/426 |
| 5,100,668 | 3/1992 | Edelman et al. | 424/422 |
| 5,116,864 | 5/1992 | March et al. | 514/455 |
| 5,171,217 | 12/1992 | March et al. | 604/53 |
| 5,290,267 | 3/1994 | Zimmermann | 604/272 |
| 5,487,739 | 1/1996 | Aebischer et al. | 604/890.1 |
| 5,575,015 | 11/1996 | Slepian et al. | 623/1 |
| 5,605,696 | 2/1997 | Eury et al. | 424/423 |

OTHER PUBLICATIONS

Edelman et al., "Effect of Controlled Adventitial Heparin Delivery on Smooth Muscle Cell Proliferation following Endothelial Injury," *Proc. Natl. Acad. Sci. USA*, Medical Sciences, May 1990, vol. 87, pp. 3773–3777.

Rogers et al., "Controlled Release of Heparin Reduces Neointimal Hyperplasia in Stented Rabbit Arteries: Ramifications for Local Therapy," *Journal of Interventional Cardiology*, Mar. 3, 1992, vol. 5, No. 3, pp. 195–202.

Rogers, et al., "Inhibition of Experimental Neointimal Hyperplasia and Thrombosis Depends on the Type of Vascular Injury and the Site of Drug Administration," *Circulation*, May 17, 1993; vol. 88, No. 3, pp. 1215–1221.

Hill, et al., "Inhibition of Thrombosis and Intimal Thickening by in situ Photopolymerization of Thin Hydrogel Barriers," *Proc. Natl. Acad. Sci. USA*, Medical Services, Jun. 1994, vol. 91, pp. 5967–5971.

Slepian, Marvin J., "Polymeric Endoluminal Paving: A Family of Evolving Methods for Extending Endoluminal Theropeutics Beyond Stenting," *Cardiology Clinics*, Nov. 1994, vol. 12, No. 4, pp. 715–737.

*Primary Examiner*—Wynn Wood Coggins
*Assistant Examiner*—N. Kent Gring
*Attorney, Agent, or Firm*—Leydig, Voit & Mayer, Ltd.

[57] ABSTRACT

Devices and methods are disclosed for the percutaneous administration of a composition to a desired in vivo location. The composition comprises a biologically active substance and a pharmaceutically acceptable carrier. The pharmaceutically acceptable carrier is preferably non-solid and a polymer, which is preferably capable of being transformed into a gel, thus allowing timed-released delivery of the substance. A preferred use for this invention is to provide local delivery of biologically active substances for the prevention of restenosis following angioplasty or other blood vessel injury.

59 Claims, 7 Drawing Sheets

TIMED-RELEASE LOCALIZED DRUG DELIVERY BY PERCUTANEOUS ADMINISTRATION

BACKGROUND OF THE INVENTION

1. Field of the Invention

The present invention relates generally to methods and devices for administering biologically-active substances for delivery to desired in vivo locations, as might be particularly useful in treating blood vessels or grafts following angioplasty procedures.

While systemic administration of drugs or other biologically-active substances is satisfactory for many medical treatments, many other treatments can be facilitated and/or improved with local drug delivery or administration to selected portions of internal body tissues. Localized drug administration is particularly advantageous where drug retention in the treated locus is required for an effective period of time without appreciably affecting other body tissues. Strictly by way of example, drug delivery to a specific locus can be desired in the treatment of cancerous tumors or the like. In the treatment of such tumors, often an objective is to administer the cancer drug so that it localizes, as much as possible, in the tumor itself in order to limit systemic toxicity.

Another exemplary treatment for which localized drug delivery is desirous involves prevention of vessel renarrowing, or restenosis, following percutaneous revascularization techniques, such as percutaneous transluminal angioplasty (PTA). Although PTA provides an alternative to bypass surgery for relieving stenosis of obstructive atherosclerotic blood vessels, the long-term success of the angioplasty is often compromised by the onset of restenosis thereby requiring reintervention. In the PTA procedure, an inflatable balloon disposed at the distal end of a catheter is positioned in the region of a stenosis. The balloon is inflated under fluid pressure to reconfigure the narrowed lumen and thereafter permit increased blood flow through the affected artery. It is not unusual that inflation-deflation cycles will be repeated several times where the narrowing is severe. This mechanical violence to the arterial wall may produce the desired opening of the artery, but in delayed consequence the procedure is followed by an estimated 25%–50% incidence of restenosis, typically within 6 months to 2 years of the procedure (depending on the location), at or near the injured site.

Studies have suggested a number of conditions which lead to vessel restenosis, including remodeling and intimal hyperplasia. These studies have indicated that vessel injury, such as endothelial denudation, injury to the vascular wall, and rupture of the vase vasorum, can result as an unwanted consequence to an angioplasty thereby making the treated site susceptible to restenosis. Upon injury, the ensuing deposition of platelets, in connection with the vessel's healing mechanism, signals smooth muscle cell proliferation within the arterial wall. The deposition of platelets may lead to acute thrombosis in some circumstances. More significantly, the proliferation of smooth muscle cells is a process which frequently continues unabated and has therefore been widely implicated as a prominent factor in the resulting restenosis. No pharmacologic or mechanical intervention has heretofore proven sufficiently effective in preventing restenosis following angioplasties.

2. Description of the Prior Art

The prior art has proposed various techniques that attempt to prevent restenosis following an angioplasty. A mechanical strategy has involved the use of stents with the hope that the radial expansile force that stents exert would restore luminal integrity and preserve maximum vessel diameter. In use, however, whereas stents have demonstrated some measure of success in limiting abrupt reclosure and remodeling following vascular intervention, stents have been quite unsuccessful in preventing the more progressive condition of restenosis. Because of their rigid nature, stents actually can induce vessel injury and hence intrastent thrombosis and restenosis.

Other approaches have focused on the administration of smooth muscle cell growth regulators. Most of these approaches have attempted to provide localized delivery inasmuch as systemic dosing through intravenous infusion or oral ingestion is inadequate because of the risk of hemorrhage and other complications. For example, Rogers et al., Circulation, 88:1215–1221 (1993), discuss the use of heparin, an inhibitor of vascular smooth muscle cell proliferation, as a way to limit neointimal hyperplasia following arterial injury. The Rogers et al. article emphasizes that more chronic and severe vessel damage demands prolonged administration of antiproliferative agents in order to attenuate the possibility of hyperplasia and restenosis. In practice, however, previous attempts to deliver antiproliferative agents have not met with success in achieving prolonged prevention of restenosis, as discussed in detail below.

Among prior art delivery approaches is the use of catheter systems to treat the primarily local vascular response to injury. In one catheter system, an inner balloon is inflated to firmly place an outer balloon of the catheter in direct contact with the vessel wall. The outer balloon of the catheter, which is in contact with the vessel, is defined by a drug transport wall which is constructed of a material that is selectively permeable and, thus, permits selective transport of a drug therethrough. For example, this drug transport wall is constructed of perforated, permeable, microporous or semipermeable material through which the drug is intended to selectively pass. Another similar catheter system contains two separated expansile portions which, when pressurized, form a space therebetween. Blood may then be removed from the space and a biologically active substance may be placed therein to come into direct contact with the vessel wall. Another catheter system for drug delivery is described in U.S. Pat. No. 5,171,217 to March et al. According to March et al., a drug carried by microparticles of a physiologically-compatible, biodegradable polymer, is intramurally injected under directed pressure into the wall of a body vessel in the region of the affected site.

These catheter delivery systems are unsatisfactory because, among other things, the catheter must reside within the blood vessel for a significant length of time, causing discomfort and inconvenience to the patient. Further, prolonged instrumentation, as is necessitated by many intraluminal devices, also increases the risk of thrombosis. Additionally, even after a significant length of time, insufficient amounts of the drug typically enter the target cells to achieve the desired result. Indeed, a significant problem with delivery of drugs via catheter systems is that the drug is diluted and carried away in the turbulent and high velocity blood stream. Accordingly, high pressure transmural perfusions from intravascular catheters merely provide transient luminal drug delivery inasmuch as lasting drug levels in the vessel have not been demonstrated. Significantly, the perfusion catheter itself produces local injury and necrosis to the endothelium and adjacent tissue, presumably as a result of the high pressures used to instill drugs, and, as such, actually induces restenosis while delivering a drug for the purpose of preventing restenosis. These procedures also add to the time, cost, complexity, pain and morbidity of, for example, post-angioplasty procedures and do not result in adequate dosage of the active substance to target cells. There is also a significant risk that systemic levels of drug will be achieved when perfusion catheters are utilized for drug delivery.

Other approaches for drug delivery have attempted to combine the mechanical support offered by stents with drug delivery. For example, Rogers and Edelman, *Journal of Interventional Cardiology*, 5:195–201 (1992), describe the use of endovascular stents containing drug-eluting coatings. This drug delivery system was devised to overcome intrastent thrombosis, a condition which plagued previous stent placement procedures. However, drug-eluting coatings do not permit a sustained reduction in smooth muscle cell proliferation. In this regard, these coated stents release most of their drug within the first hours of deployment and do not provide penetrating delivery to the vessel wall for a prolonged period of time. Another approach is found in Slepian, *Contemporary Interventional Techniques*, 12:715–737 (1994), which describes time-limited endoluminal wall support in the form of polymeric endoluminal paving. In this system, tubes or sheets of biodegradable drug delivery polymers are transported intraluminally via a catheter system and locally thermoformed, yielding supportive, thin polymeric endoluminal liner layers. This type of drug delivery is also unsatisfactory because it requires placement using a catheter, does not yield prolonged drug delivery, and is associated with a significant increase in the time, cost, complexity, pain and morbidity of related procedures.

Similarly, Hill-West et al., *Proc. Natl. Acad. Sci.*, 91:5967–5971 (1994), describe the application of hydrogel barriers that are provided on the inner surface of injured arteries. According to Hill-West et al., the barrier can be used for the controlled release of macromolecular drugs. As the gel loosens by degradation, the drug is slowly released. This approach likewise suffers from an inadequate residence time because much of the drug that is delivered dissolves downstream away from the desired localized site. The proposal identified by Hill-West et al. is also greatly restrained inasmuch as drug delivery is not possible after the gel dries.

Yet another type of localized drug delivery is described in Edelman et al, *Proc. Natl. Acad. Sci.*, 87:3773–3777 (1990). Edelman et al. discuss site-specific therapy following vascular interventions in which ethylene/vinyl acetate copolymer matrix is utilized to permit heparin delivery over time. In practice, however, the approach described by Edelman et al. is ill-suited for treating restenosis in vivo because the matrices must be surgically deployed. Because angioplasties and other intravascular interventions demonstrate value by producing desired results while obviating the need for open operation, the performance of an operation to improve the results of an intravascular intervention negates the clinical value of that interventional procedure.

Despite the availability of the foregoing prior art approaches, it will be appreciated that there still exists a need in the art for a method of localized drug delivery which does not require a surgical procedure and which delivers a drug in a timed-release fashion wherein the drug delivery is sustained in its desired localized site. For example, there exists a specific need for localized drug delivery to blood vessels or grafts in order to inhibit the onset of restenosis following angioplasty or other intravascular interventions in which the drug delivery is released over time and wherein the drug does not get carried away in the blood stream or get undesirably diluted therein. There also exists a need for drug delivery to blood vessels or grafts in which a vessel's lumen and endothelium are not subject to injury and in which a surgical procedure is not required.

SUMMARY OF THE INVENTION

The aforesaid problems are solved, in accordance with the present invention, by methods and devices for percutaneously administering sustained, timed-release localized drug delivery of biologically active substances to desired in vivo locations. One aspect of the present invention relates to the methods of drug delivery. Administration of compositions described herein is accomplished by delivering to the desired locus a composition comprising a biologically active substance and a pharmaceutically acceptable carrier. The pharmaceutically acceptable carrier is preferably a polymer, for example, a polysaccharide such as alginate. Although the carrier can be in the form of a solid, preferred carriers are non-solid. More preferably, the non-solid carrier is compatible with a cross-linker which converts the first composition into a less mobile gel or solid.

The methods of the present invention can be utilized with any desired in vivo locus, such as a vessel, organ, tissue or cavity that can be percutaneously treated. The desired locus can be treated under the methods of the present invention by delivering biologically active substances into, around, or adjacent to the locus, as desired. By way of example, in one embodiment the methods of drug delivery under the present invention can be utilized to treat a blood vessel or graft that has been subject to an endovascular procedure, for example, an angioplasty or stent placement, by providing biologically active substances substantially around the vessel or graft without intramurally entering the interior thereof. Specifically, biologically active substances, including, but not limited to, drugs such as heparin (including modified forms of heparin such as NAC-heparin) can be injected into a periadventitial area of the blood vessel or graft that has been subject to the angioplasty without traversing the endothelium and lumen of the vessel. For clarity of description, the term "periadventitial" is meant to include the adventitia of a vessel, as well as soft tissues near the adventitia. The biologically active substances are injected nonintramurally, meaning that the injection does not traverse the endothelium and lumen, although the substances may diffuse to an intramural location subsequent to the injection. Significantly, the methods under the present invention do not create further injury to blood vessels, particularly the lumen and endothelium, and therefore do not promote the onset of restenosis. In addition, the novel percutaneous methods of the present invention do not require a surgical procedure.

Another aspect of the present invention relates to a device for administering biologically active substances to a desired in vivo locus unintrusively and quickly. The device is of a tubular configuration and is capable of delivering compositions by injection. The tubular member has at least one lumen therethrough. Although the tubular member can be of a substantially linear configuration, the tubular member can alternatively comprise a first section which lies along a longitudinal axis of the member and a second section which lies substantially along an arc, and terminates in a piercing part having at least one lumen opening for the passage of predetermined selected compositions.

Percutaneous administration of compositions, for example to the periadventitial surface of a blood vessel or graft, yields several advantages. For example, percutaneous administration is simpler and faster than surgical deployment, requiring only a tubular member and syringe. The present invention is less painful to the patient, as it can be done entirely under local anesthesia at the time of the primary procedure, whether it involves an angioplasty, atherectomy, the stenting of arteries, veins, bypass grafts or dialysis grafts or other endovascular procedure, leaving only a puncture site rather than an incision. Further, percutaneous administration under the present invention is less likely to result in complications such as wound infection or injury to surrounding tissues. These compositions would also be amenable to use at the time of surgical creation of bypass or dialysis grafts, applied directly to the adventitial surface of the blood vessel or outside surface of the graft.

The present invention will be more fully understood upon reading the following detailed description of the preferred embodiments in conjunction with the accompanying drawings.

BRIEF DESCRIPTION OF THE DRAWINGS

Although the characteristic features of this invention will be particularly pointed out in the claims, the invention itself, and the manner in which it may be made and used, may be better understood by referring to the following descriptions taken in connection with the accompanying drawings forming a part hereof, wherein reference numerals refer to like parts throughout the several views.

DETAILED DESCRIPTION OF THE PREFERRED EMBODIMENTS

The following portion of the specification, taken in conjunction with the drawings, sets forth the preferred embodiments of the present invention. The embodiments of the invention disclosed herein include the best mode contemplated by the inventor for carrying out the invention in a commercial environment, although it should be understood that various modifications can be accomplished within the parameters of the present invention.

The present invention relates to percutaneous administration of a composition comprising a biologically active substance and a carrier, preferably a polymeric carrier, to any desired locus within the body. Although the following discussion relates to administering biologically active substances to blood vessels or grafts, it is understood that this discussion is merely illustrative, and the drug delivery of the present invention can be applied to other locations within the body.

Figure 1:
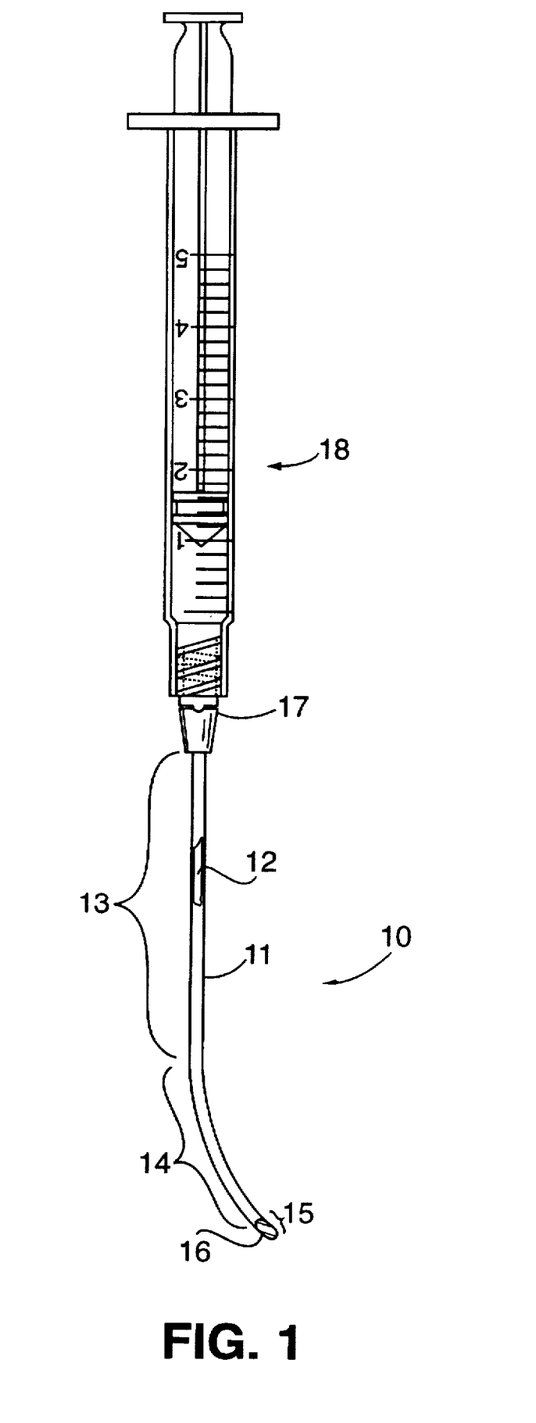
FIG. 1 is a side elevation view of an embodiment of a slender, tubular device according to the present invention shown in conjunction with a syringe, having a cut-out cross-sectional view depicted therein.

Referring now to the drawings, FIG. 1 illustrates an exemplary embodiment of a slender, tubular member or device 10, in accordance with the present invention. In general, this embodiment provides a means and a system for delivering a composition comprising a biologically active substance and a pharmaceutically acceptable carrier to a specific desired body locus, such as a blood vessel or graft. This delivery mechanism provides for treatment of a localized area of the locus or treatment of a localized area of tissue adjacent thereto, with minimal, if any, undesirable effects on other body tissues.

The tubular device 10 of this embodiment comprises a hypodermic needle 11 having a lumen 12 therethrough. This embodiment includes a first section 13 that is substantially linear and which lies along a longitudinal axis of the hypodermic needle 11, and a second section 14 which is fluidly connected to the first section and which curves substantially along an arc. The second section 14 terminates in a piercing part 15 which contains a lumen opening 16. One of ordinary skill in the art will appreciate that a hub 17 can be provided to selectively couple the needle 11 with a syringe 18. Stopping means, for example in the form of an obturator (not shown), can be provided to preclude release of substances at a premature or otherwise undesired time and to prevent plugging of the device 10. Devices 10 according to the present invention are made using standard manufacturing practices and are preferably used according to inventive methods described herein.

Figures 2, 3:
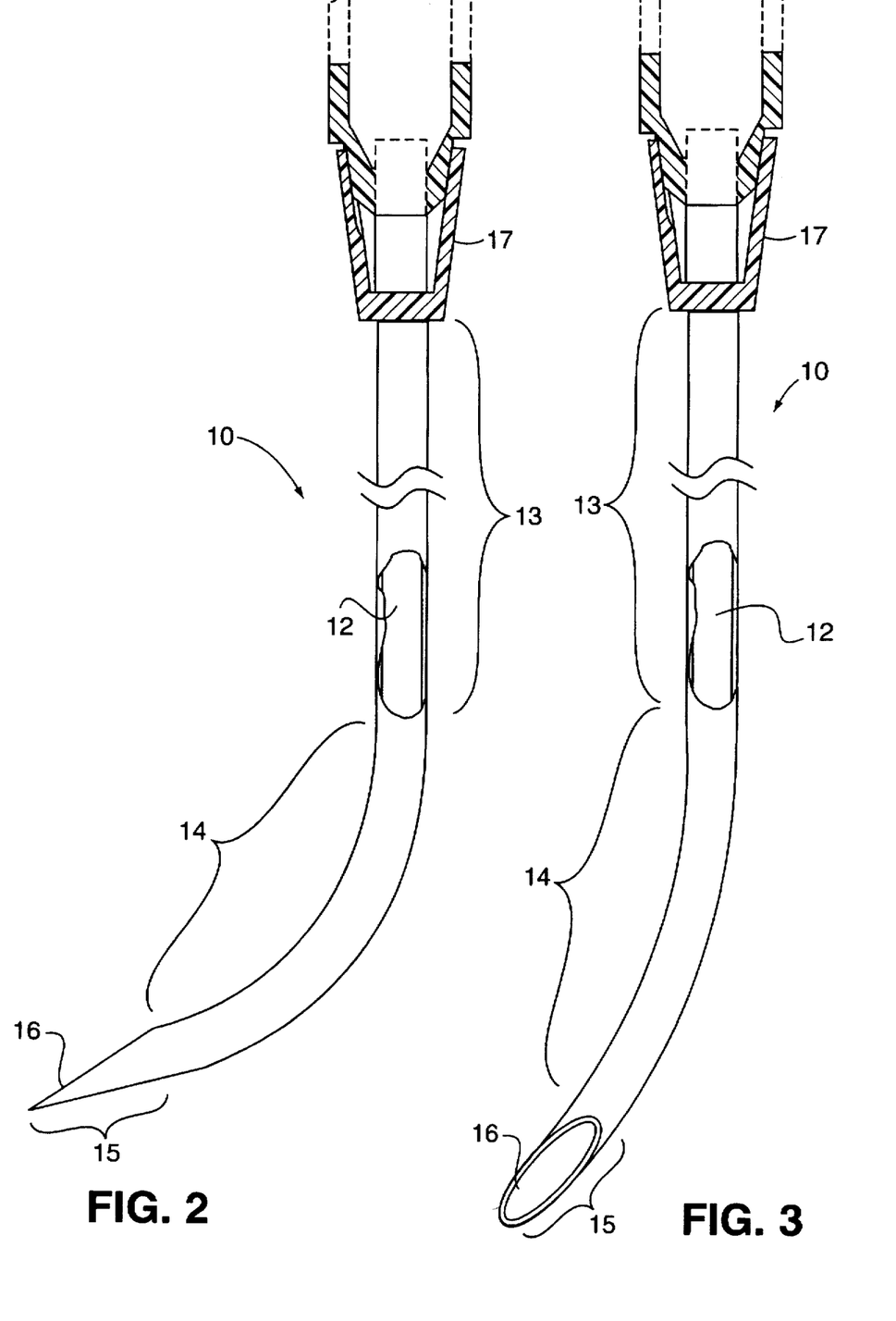
FIGS. 2 and 3 represent side elevation views of alternative embodiments of tubular devices according to the present invention, having cut-out cross-sectional views depicted therein.
Figure 4:
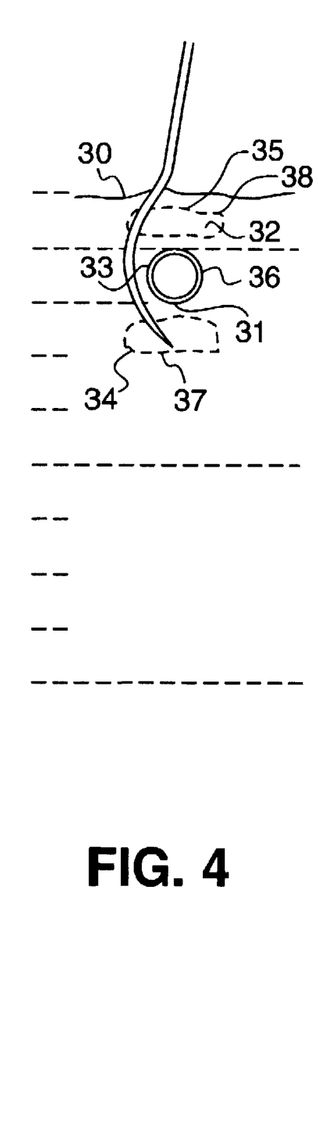
FIG. 4 is a cross-sectional view of a blood vessel or graft and a side view of an embodiment of a tubular device according to the present invention, illustrating a preferred relationship between a blood vessel or graft and an inventive tubular device in exemplary use according to inventive methods and also illustrating various regions in a periadventitial area of the blood vessel or graft.
Figure 5:
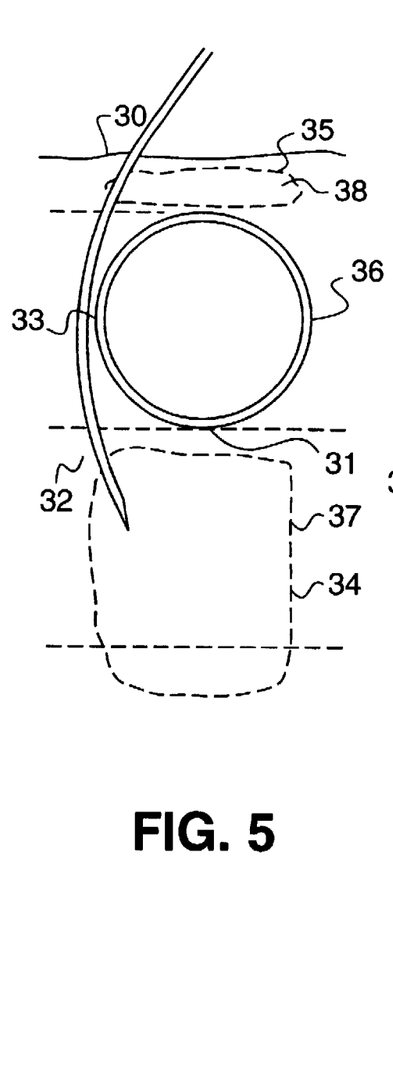
FIGS. 5–7 are cross-sectional views of blood vessels or grafts and side views of alternative embodiments of inventive tubular devices, preferably used for exemplary applications relating to blood vessels of different sizes and at different depths beneath the patient's skin.
Figure 6:
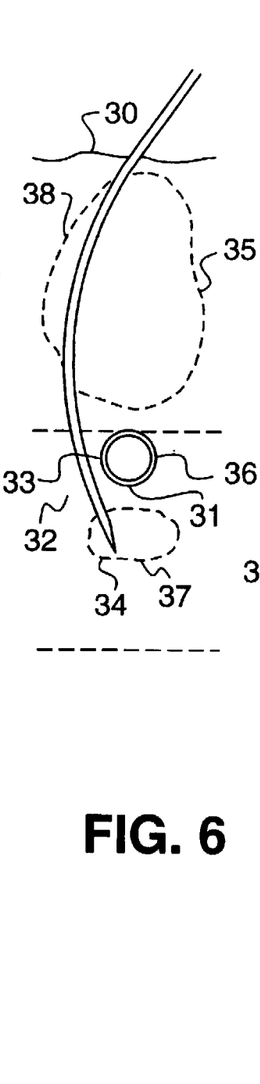
Figure 7:
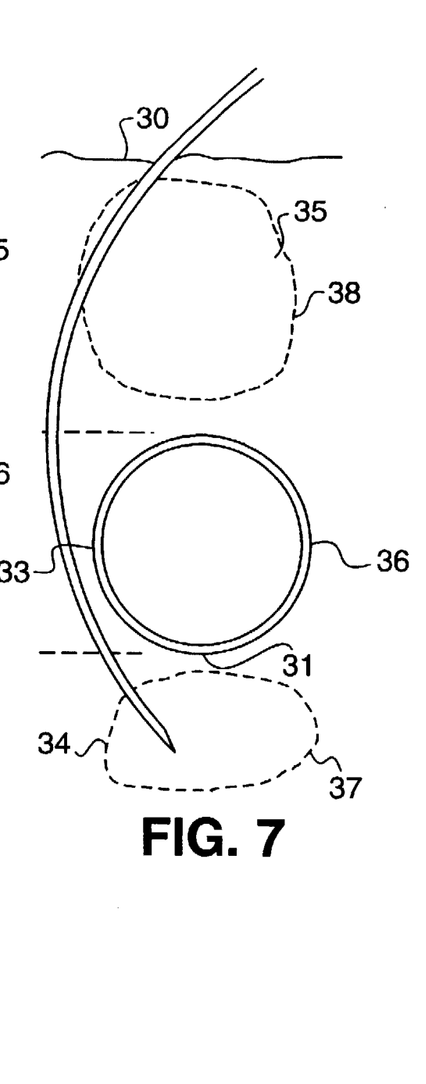
Figure 8:
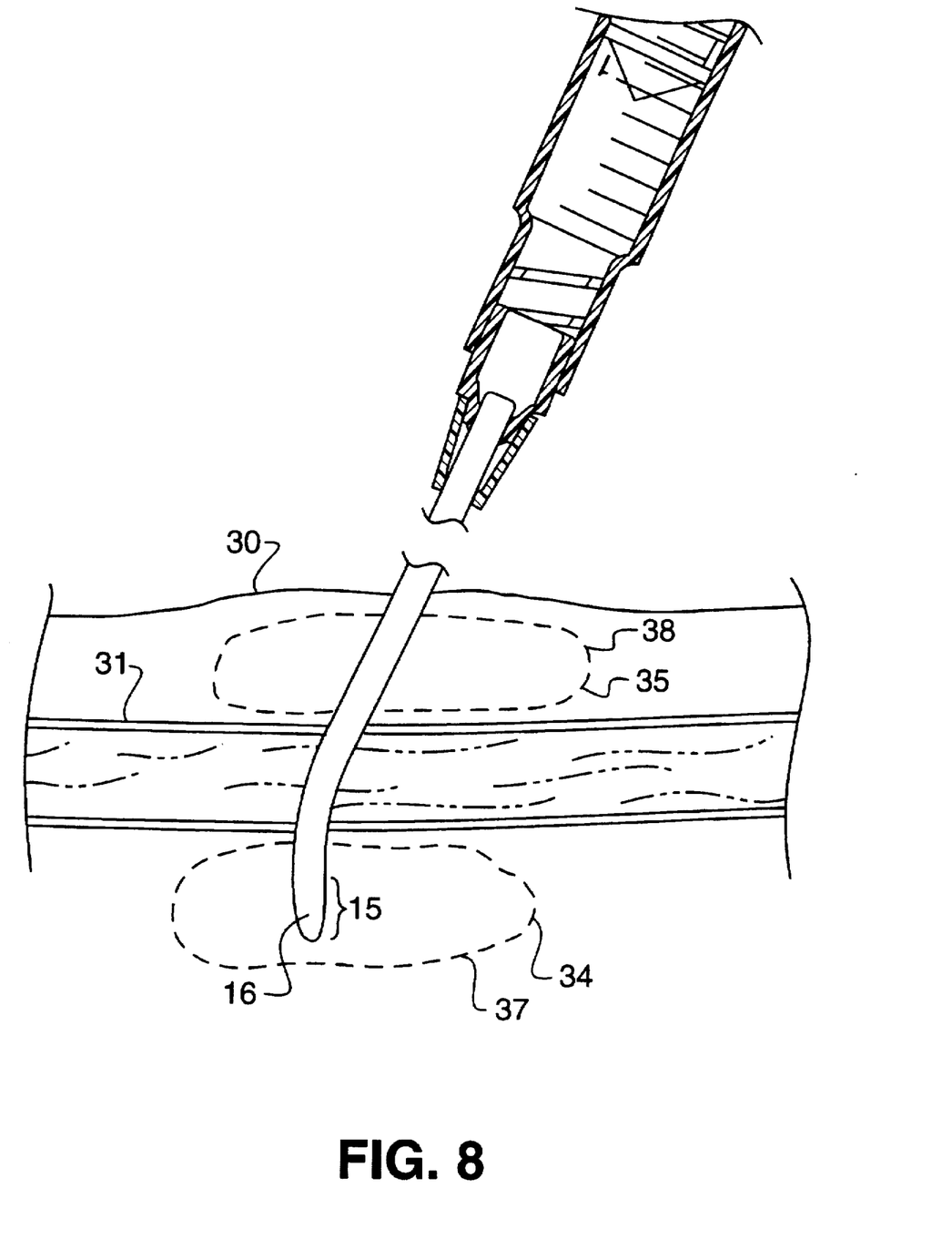
FIG. 8 is a longitudinal cross-sectional view of a blood vessel or graft and a front view of an embodiment of a tubular device according to the present invention.
Figure 9:
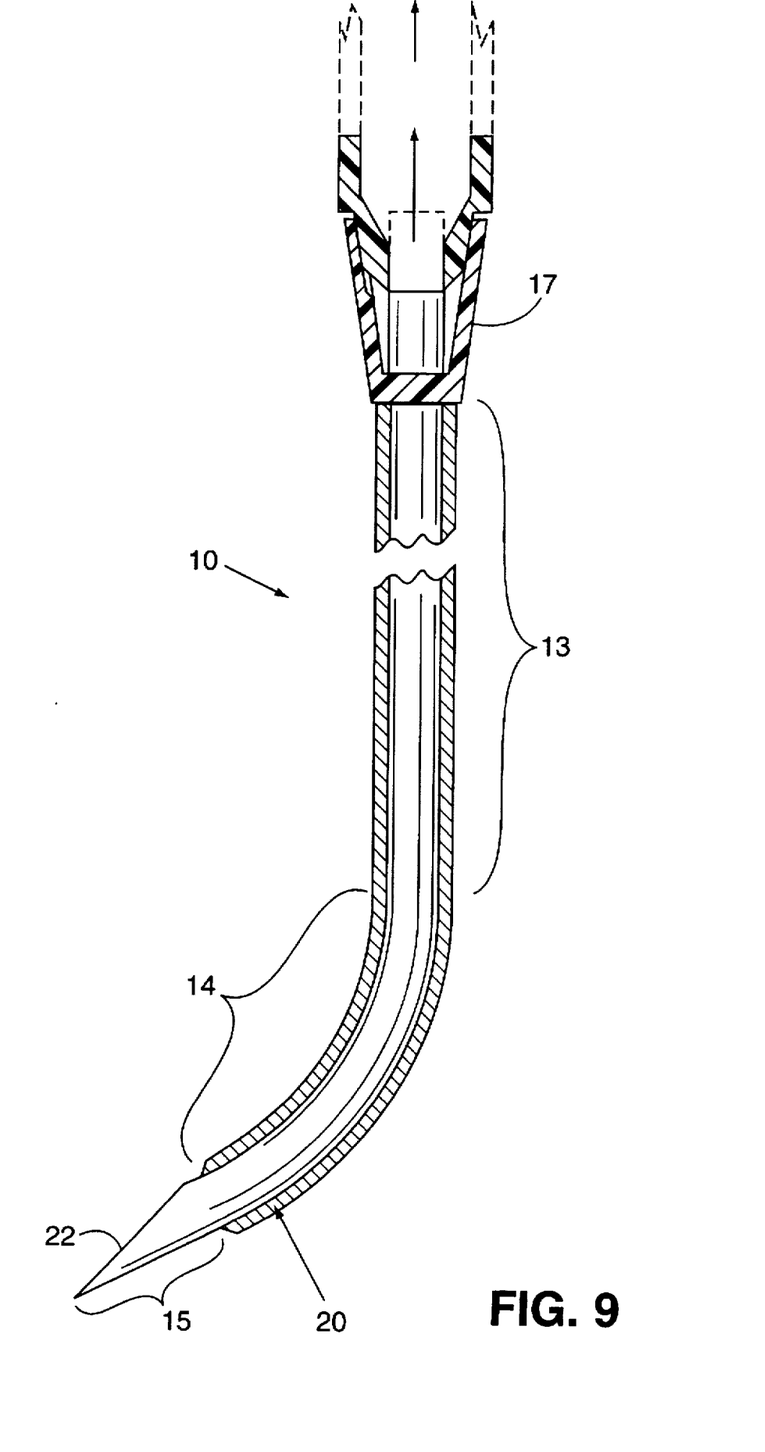
FIG. 9 represents a side elevation view of an alternative embodiment of a tubular device comprising a cannula and a trocar in accordance with the present invention.

Alternative embodiments of devices 10 under the present invention are depicted in FIGS. 2–3 and 9. In FIG. 2, the piercing part 15 of the hypodermic needle 11 is oriented such that the lumen opening 16 faces substantially toward the interior of a circle or ellipse defined by the arc of the second section 14, termed "curved section" herein. Alternatively, FIG. 3 depicts an embodiment wherein the lumen opening 16 faces in a direction not lying within the plane of a circle or ellipse defined by the arc. It can readily be seen by one of ordinary skill in the art that the lumen opening 16 could alternatively face away from the interior of the circle or ellipse in a direction substantially in a plane defined by the circle or ellipse or in any other direction rotated around the hypodermic needle 11.

As seen in FIG. 9, a preferred embodiment of the device 10 comprises a cannula 20 encasing a trocar 22 which contains the piercing part 15. This telescoping arrangement is advantageous because of the additional support offered by the trocar 22. The trocar 22 can be selectively removed to permit injection of substances as desired. The combination of the cannula 20 and trocar 22 shown in FIG. 9 is a preferred alternative to the unitary hypodermic needle 11 shown in FIGS. 1-3. It is noted that the preferred device 10 shown in FIG. 9 can be constructed in various arrangements with regard to the position of the lumen opening 16, including either embodiment shown in FIGS. 2 and 3.

Referring now to the embodiments depicted in FIGS. 4-7, the curved section 14 is configured such that, when inserted into a patient's skin 30 directly above a blood vessel or graft 31, it can be advanced around a first side 33 of the blood vessel or graft 31 to a point substantially overlying the blood vessel or graft 31 opposite the skin 30. As such, it can be readily seen by one skilled in the art that curved sections 14 having various radii and having various arc lengths would be appropriate for use associated with various blood vessels or grafts having different diameters and depths beneath the skin.

The dimensions of the preferred device will vary depending upon the type of application and its location. For example, brachial arteries and dialysis conduits are often only a few millimeters under the skin in thin people, whereas femoral arteries may be 10 centimeters or more under the skin in obese people. Diseased radial, ulnar, tibial or peroneal arteries may be only 1 or 2 millimeters in diameter, whereas large femoral arteries or axillary veins may be over 8 millimeters in diameter. It can readily be seen that the curved section 14 of an inventive device 10 to be used to treat radial or dorsalis pedis arteries, which have very small diameters and which are very close to the skin, would have a relatively small radius and a relatively small arc length. By way of contrast, a preferred device 10 for use associated with the deeper femoral artery, which has a relatively large diameter and is relatively deep beneath the skin, would comprise a curved section 14 having a relatively large radius and a relatively large arc length.

It can readily be seen that a tubular device 10 formed according to the present invention must have a gauge which offers sufficient rigidity to maintain the appropriate arc. In addition, it can be readily seen that the preferred gauge "g" of the device 10 will be dependent upon the viscosity of the injected composition. As such, a device 10 smaller than about 21 g would likely clog too easily, and may fail to retain the appropriate arc in use. A preferred device 10 of the present invention, therefore, has a gauge from about 21 g to about 18 g. More preferably, the tubular device 10 has a gauge from about 20 g to about 19 g.

The inventive device 10 described above is preferably used for administering a biologically active substance to the specific desired locus within the body, such as a periadventitial surface of a blood vessel or graft 31 in vivo. Preferably, the substance is administered by delivering to the periadventitial area overlying the blood vessel or graft 31 in vivo a composition comprising a biologically active substance and a pharmaceutically acceptable carrier for releasing the substance over a period of time. Most preferably, the composition is delivered substantially completely around the blood vessel or graft in relatively close proximity to the adventitial surface of the blood vessel or graft. Ideally, a ring would be formed substantially around the periadventitial surface; however, it can readily be seen that placing the composition reasonably near the periadventitial surface will achieve the desired result of delivering active substances to cells of the vessel wall or cells adjacent to a graft.

Referring again to FIGS. 4-7 and FIG. 8, for treatment of a blood vessel or graft 31 according to an exemplary utility for the present invention, the device 10 is preferably advanced under a patient's skin 30 such that the piercing part 15 of the device 10 moves around a first side 33 of the blood vessel or graft 31 to a first location 34 in the periadventitial area of the blood vessel or graft 31. The first location 34 is preferably opposite the blood vessel from the skin 30. Next, the composition is injected through the lumen opening 16 as the piercing part of the tubular device 10 is withdrawn from the first location 34 to a second location 35. A second location 35 is preferably between the blood vessel or graft 31 being treated and the patient's skin 30. Next, the device 10 is advanced such that the piercing part 15 moves around a second side of the blood vessel or graft 31 to a third location 37. This third location 37 is preferably near the first location 34. Next, the composition is injected through the lumen opening 16 as the piercing part 15 is withdrawn from the third location 37 to a fourth location 38 which is substantially the same as the second location 35. The device 10 may then be withdrawn from the skin 30.

It is noted that the above method may be usefully performed using a linearly straight tubular device in accordance with the present invention. In a preferred embodiment, however, an inventive device 10 having a curved section 14 is used. A curved device 10 with the appropriate radius, as described hereinabove, can be advanced through a single puncture site around a blood vessel, closely hugging the perimeter of that vessel. As the device 10 is withdrawn, the polymer can be administered closely to the outer surface, the adventitia, of that blood vessel. Without removing the device 10 completely from the patient, the device 10 can be rotated 180° and advanced around the other side of the blood vessel, allowing introduction of the polymer on that side. It would be more difficult to remain close to the adventitia of the blood vessel if a straight tubular device were used. In this embodiment, the most preferred device 10 would be one having a radius and an arc length capable of delivering the composition closely to the deepest wall of the vessel or graft 31 from a single percutaneous puncture.

As mentioned above, the composition being injected preferably comprises a biologically active substance and a pharmaceutically acceptable carrier for releasing a substance over a period of time. The biologically active substance may include, for example, a gene, a gene regulator, an antibody, a polypeptide, a radioactive composition, or a drug. Examples of drugs which are preferably used in accordance with the present invention in the context of blood vessels or grafts are heparin, hirudin, an enzyme inhibitor, estrogen, and angiopeptin. These lists, however, are not intended to be exhaustive, and the present invention contemplates a wide variety of substances which serve as useful biologically active substances depending upon the locus and particular treatment involved.

Although the pharmaceutically acceptable carrier of the present invention may be any of a wide variety of pharmaceutically acceptable carriers, a preferred carrier is a polymer. In addition, although solid carriers, including but not limited to microcapsules, that are capable of being injected by a tubular device 10 can be utilized under the present invention, the carrier is preferably "non-solid." As used herein, the term "non-solid carrier" is intended to refer to a carrier which has physical characteristics similar to a liquid or a gel and which is capable of being injected through a tubular device 10. In a preferred embodiment, the pharmaceutically acceptable non-solid carrier is a liquid polymer capable of being cross-linked and thus converted into a gel or a solid upon being mixed with a suitable cross-linker. As used herein, the term "cross-linker" is meant to refer to a substance which, when mixed with a specific non-solid polymer, will cause the non-solid polymer to be converted to a gel or solid. In accordance with this embodiment, the cross-linker is preferably delivered into the periadventitial area simultaneously with or subsequent to the delivery of the first composition. Most preferably, the first composition and the cross-linker are delivered by injection through a tubular device 10 under the present invention.

In one preferred embodiment, the polymer is a polysaccharide. More preferably, the polymer is one capable of being cross-linked when mixed with a cross-linker as noted above. One example of a polymer capable of being cross-linked is alginate, and preferred cross-linkers for use therewith include divalent cations such as calcium, for example in the form of calcium chloride or calcium gluconate. The desired effect may be obtained with regard to alginate by using as a cross-linker a wide variety of divalent cations However, various divalent cations have different effects upon the gel, the substance carried therein, and the surrounding tissue. As such, the preferred divalent cations selected for a particular use will depend on the carrier being used, the substance being delivered, and the specific in vivo location of the delivery.

The term "alginate" as used herein is intended to designate a family of unbranched binary copolymers of 1-4-linked β-D-mannuronic acid (M) and α-L-guluronic acid (G). Alginates have widely varying compositions and sequences, depending on the organism and the tissue from which they are isolated. The monomers are arranged in a pattern of blocks along the chain, with homopolymeric regions (termed M and G blocks) interspersed with regions of alternating structure (MG blocks).

Thus, when inventive methods are used to deliver a composition comprising a biologically active substance, as most preferably carried in a pharmaceutically acceptable non-solid polymer capable of being cross-linked, to a desired location such as the periadventitial area overlying the blood vessel or graft in vivo, a subsequent injection of a cross-linker causes the first non-solid composition to be converted to a gel or a solid, thereby advantageously becoming more apt to remain immobilized. Accordingly, a preferred method for treating a blood vessel or graft in vivo with the biologically active substance comprises a non-solid carrier and additionally comprises injecting a second non-solid composition into the first non-solid composition, wherein the second non-solid composition comprises a cross-linker, prior to withdrawing the piercing part 15 of the tubular device 10 from the skin.

Figure 10A:
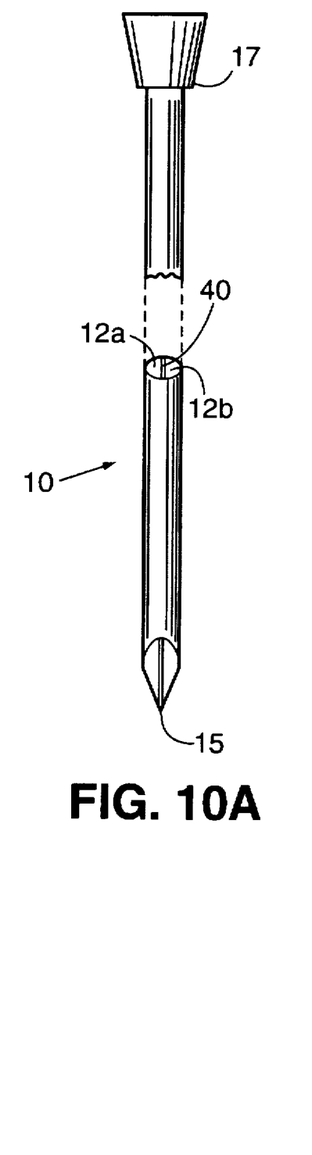
FIG. 10A represents a front elevation view of an exemplary embodiment of a linear tubular member comprising two lumens having a cut-out cross-sectional view therein to show an internal section in accordance with the present invention.
Figure 10B:
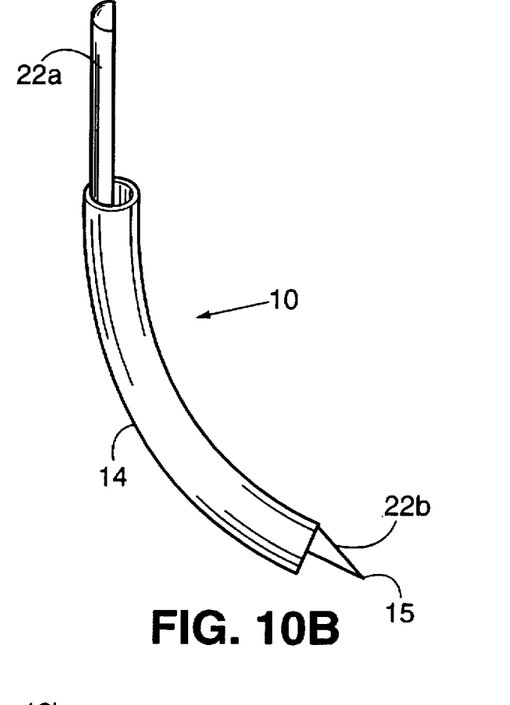
FIG. 10B represents a side elevation view of an exemplary embodiment of a curved tubular member broken away to reveal two trocars for use with two lumens in accordance with the present invention.

Additionally contemplated by this invention are methods and devices for injecting the first composition and a cross-linker simultaneously. As seen in FIGS. 10–13, in a preferred method a tubular device 10 is used which has more than one lumen 12a and 12b, and is thus capable of injecting the first composition and the cross-linker simultaneously. For example, FIGS. 10A and 10B depict a first exemplary arrangement of a tubular member 10 which comprises two substantially semicircular (in cross-section) lumens 12a and 12b disposed side-by-side separated by a septum 40. Septum 40 isolates the two lumens 12a and 12b into separate chambers thereby permitting segregated simultaneous flow of different compositions, as desired, without premature mixing thereof. Septum 40 can terminate at or near the piercing part 15 so that the first composition and the cross-linker can be mixed after or just before they exit at least one lumen opening.

FIG. 10A illustrates the side-by-side lumens 12a and 12b in a linear tubular member 10, while FIG. 10B shows the side-by-side lumens 12a and 12b in a curved tubular member 10. As seen in FIG. 10B, a pair of trocars 22a and 22b can be disposed in corresponding lumens if desired, although placing a trocar in only one lumen is also possible. The trocars 22a and 22b for the side-by-side arrangement are preferably substantially configured in a D-shape so as to be particularly compatible with the semicircular lumens 12a and 12b. It will be appreciated that the two D-shaped trocars 22a and 22b can form a conical or pyramidal piercing portion 15, although each trocar can be configured to form a conventionally shaped piercing portion, which is particularly useful if only one trocar is desired.

Figure 11A:
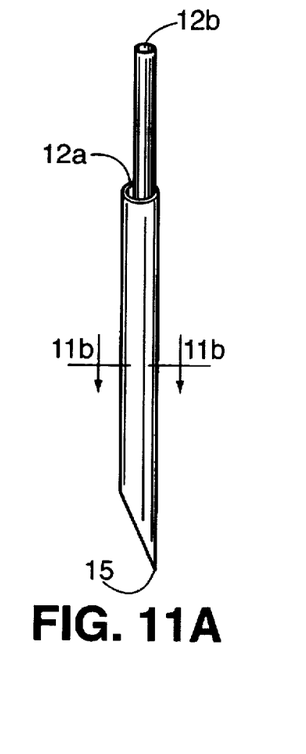
FIG. 11A represents a side elevation view of an alternative embodiment of a tubular member comprising two lumens, broken away to reveal outer and inner lumens in accordance with the present invention.
Figure 11B:
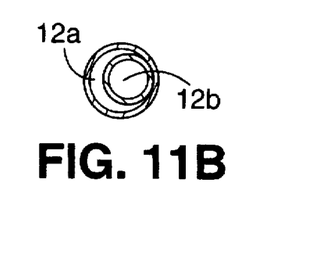
FIG. 11B represents a cross-sectional view of the tubular member depicted in FIG. 11A, taken along the line 11B—11B.

FIGS. 11A–11B depict an alternative double-lumen arrangement comprising an outer lumen 12a and an inner lumen 12b. For convenience in manufacture and use, the outer and inner lumens 12a and 12b in cross-section can preferably be fixed along a line tangent to both lumens 12a and 12b, as best seen in FIG. 11B. However, the inner lumen 12b can alternatively be wholly contained within a perimeter of the outer lumen 12a if desired. The inner lumen 12b is more readily conducive to receiving a trocar, if desired, than the outer lumen 12a, which can be, for example, moon-shaped. By using a singular trocar with inner lumen 12b while not utilizing a trocar with outer lumen 12a, the structural support provided by the singular trocar can be sufficient even in a double-lumen arrangement. It is emphasized for clarity of description that the alternative side-by-side and inner/outer double-lumen arrangements can be used in both linear and curved tubular members in accordance with the present invention. One of ordinary skill in the art will also appreciate that the alternative double-lumen arrangements can also be utilized with unitary tubular members comprising, for example, a hypodermic needle, or with cannula/trocar arrangements as described hereinabove. Also, the position of the lumen opening can vary as described above in conjunction with FIGS. 2–3.

Figure 12:
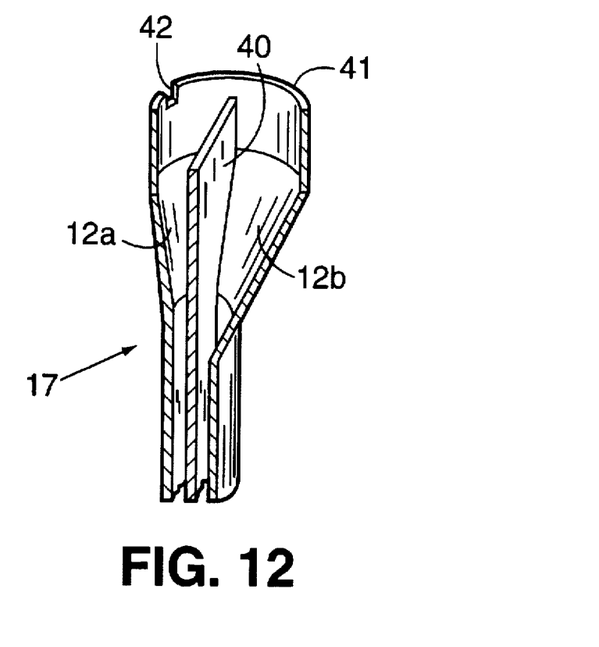
FIG. 12 represents a cross-sectional perspective view of an upper end of the embodiment shown in FIG. 10.

Referring to FIG. 12, the septum 40 preferably fully extends to a top 41 of the hub 17, or axially adjacent thereto, for the side-by-side arrangement shown in FIGS. 10A and 10B. By extending the septum 40, isolation of the lumens 12a and 12b is optimized thereby protecting separated compositions from premature mixing as desired compositions are received by the lumens 12a and 12b, for example, through corresponding receiving portions in the hub 17 or directly. The hub 17 is also preferably provided with locking means such as a notch 42 that can fit with, for example, a predetermined closure, syringe or other object having, for example, a protrusion which aligns with or otherwise matches the notch 42. The locking means prevents an opportunity for an undesired syringe or cap to engage with an unintended lumen in the tubular member.

Figure 13:
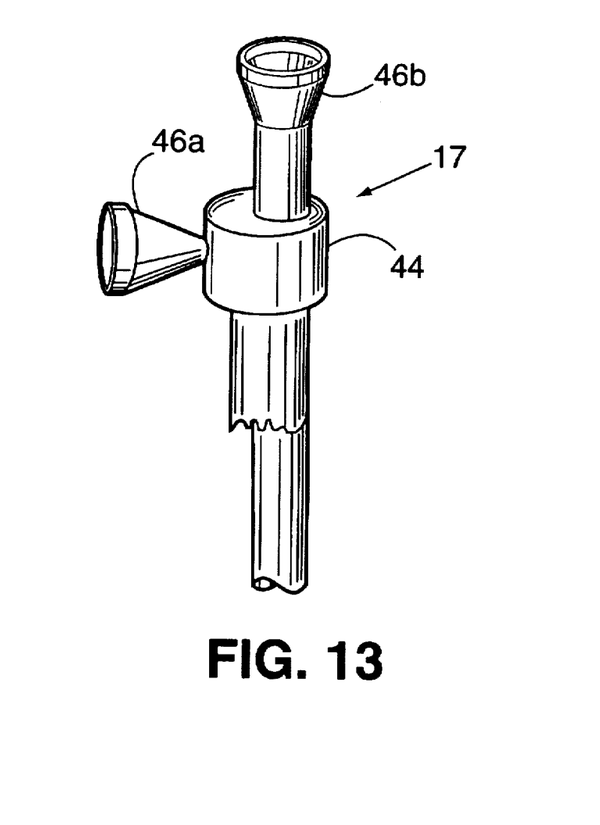
FIG. 13 represents a perspective view of a head piece for coupling the embodiment of the tubular member depicted in FIG. 11A to, for example, syringes.

As seen in FIG. 13, a preferred hub 17 for use with the outer/inner lumens 12a and 12b shown in FIGS. 11A and 11B comprises a head portion 44 including receiving portions 46a and 46b which are adapted to receive a syringe, another source for desired compositions, or a closure. The receiving portion 46b that corresponds to the inner lumen 12b vertically extends from head 44 and, as noted above, can selectively retain a trocar if desired. The receiving portion 46a that corresponds to the outer lumen 12a extends horizontally or laterally from head 44 and is therefore substantially perpendicular relative to receiving portion 46b. It will be appreciated that placement of a trocar is inconvenient in receiving portion 46a, and hence outer lumen 12a, because of this lateral placement.

As an illustration of a specific use of the inventive devices and methods, after a patient undergoes an angioplasty, stenting or other endovascular procedure of an artery, vein, or a graft, the patient's skin overlying that vessel will be sterilely prepped and draped if it is not already within the sterile field while the patient remains in the procedural suite. An inventive curved tubular member or device 10 is advanced through the skin overlying the vessel at the selected site, around the vessel to the portion of the vessel furthest from the skin. In accordance with the preferred constructed embodiment of the present invention, the inner trocar 22 of the device 10 is removed, and the first composition is injected as the trocar 22 is withdrawn. The device 10 is withdrawn to a location adjacent the skin, but not completely out of the patient. The device 10 is turned 180°, advanced around the other side of the vessel, and the first composition is introduced on this side of the vessel as well. A cross-linker is injected into the first composition, if needed, and the device 10 is completely removed from the patient. The patient can then be immediately discharged from the procedural suite with very little time having been spent undergoing time-consuming procedures and observation previously associated with the threat of restenosis. The polymer allows timed-release of the drug with predetermined optimal release kinetics. Since the administered drug would be in the soft tissues immediately surrounding the vessel, such as the adventitia, as opposed to the lumen and endothelium, the drug would not be washed quickly away, in contradistinction to the currently available intraluminal methods of drug administration.

While the preferred embodiments of the invention have been disclosed, it should be appreciated that the invention is susceptible to modification without departing from the spirit of the invention or the scope of the subjoined claims. As noted above, the present invention can be directed to any locus in the body, and is not limited to application to blood vessels and grafts. For example, the present invention can be used to percutaneously administer a biologically active substance and a carrier, preferably a non-solid carrier that is compatible with a cross-linker, into, around and/or adjacent to the desired locus, as desired, as perhaps to provide localized drug delivery to a tumor located within an organ.

What is claimed is:

1. A method for percutaneously administering localized delivery of a biologically active substance to a desired location in vivo comprising the steps of:
   a) selecting an internal locus for treatment;
   b) providing, percutaneously and nonintramurally, a hollow tubular member; and
   c) injecting through the tubular member a first composition comprising (i) a biologically active substance, and (ii) a pharmaceutically acceptable carrier for releasing the substance over a period of time, to a position adjacent to, or in the adventitia of, the selected locus in vivo.

2. A method as defined in claim 1, wherein the pharmaceutically acceptable carrier comprises a polymer.

3. A method as defined in claim 2, further comprising the step of administering a second composition to substantially the same location as the first composition.

4. A method as defined in claim 3, wherein the second composition is non-solid and comprises a cross-linker.

5. A method as defined in claim 2, wherein the polymer comprises a polysaccharide.

6. A method as defined in claim 5, wherein the polysaccharide comprises alginate.

7. A method as defined in claim 1, wherein the pharmaceutically acceptable carrier is a non-solid.

8. A method as defined in claim 1, wherein the first composition comprises at least one biologically active substance which is selected from the group consisting of a gene, a gene regulator, an antibody, a polypeptide, a radioactive composition, a drug or any combination thereof.

9. A method as defined in claim 8, wherein the biologically active substance includes a drug which comprises heparin.

10. A method as defined in claim 8, wherein the biologically active substance includes a drug which comprises hirudin.

11. A method as defined in claim 8, wherein the biologically active substance includes a drug which comprises an enzyme inhibitor.

12. A method as defined in claim 8, wherein the biologically active substance includes a drug which comprises estrogen.

13. A method as defined in claim 8, wherein the biologically active substance includes a drug which comprises angiopeptin.

14. A method as defined in claim 1, in which said injecting step comprises percutaneously injecting through a curved tubular member.

15. A method as defined in claim 14, in which the tubular member comprises a cannula and a trocar.

16. A method as defined in claim 15, wherein the curved tubular member comprises a lumen opening and a piercing portion and wherein said injecting through a curved tubular member comprises the steps of:
   a) advancing the curved tubular member around a first side of the locus to be treated to a first location substantially overlying the locus, the tubular member being capable of delivering a first non-solid composition; and
   b) injecting the first non-solid composition through the lumen opening as the piercing part is withdrawn from the first location to a second location.

17. A method as defined in claim 16, further comprising the steps of:
   c) turning the tubular member about 180°;
   d) advancing the tubular member such that the piercing part of the tubular member moves around a second side of the locus to a third location substantially near the first location; and
   e) injecting the first non-solid composition through the lumen opening as the piercing part is withdrawn from the third location to a fourth location substantially the same as the second location.

18. A method as defined in claim 17, further comprising the step of injecting a second non-solid composition into substantially the same locations as the first non-solid composition.

19. A method as defined in claim 18, wherein the tubular member comprises at least two lumens and wherein the first and second compositions are injected substantially simultaneously therefrom.

20. A method as defined in claim 18, in which the pharmaceutically acceptable non-solid carrier comprises a polymer, and wherein the second non-solid composition comprises a cross-linker.

21. A method as defined in claim 17, wherein the locus comprises a blood vessel or graft.

22. A method as defined in claim 21, wherein the second location and the fourth location are between the blood vessel or graft and the skin.

23. A method as defined in claim 21, wherein the first location and the third location are substantially opposite the blood vessel or graft from the second location and the fourth location.

24. A method as defined in claim 16, further comprising the step of injecting a second non-solid composition into substantially the same locations as the first non-solid composition.

25. A method as defined in claim 24, wherein the tubular member comprises at least two lumens and wherein the first and second compositions are injected substantially simultaneously therefrom.

26. A method as defined in claim 16, wherein the locus comprises a blood vessel or graft.

27. A method as defined in claim 1, wherein the tubular member comprises:

a) at least one lumen therethrough, b) a first section which lies along a longitudinal axis of said tubular member, and c) a second section fluidly connected to the first section, the second section lying substantially along an arc and terminating in a piercing part comprising at least one lumen opening therein.

28. A method for preventing restenosis of a blood vessel or graft comprising the steps of:

a) selecting a blood vessel or graft for which prevention of restenosis is desired; and b) delivering to a periadventitial area of the blood vessel or graft in vivo a first composition comprising (i) a biologically active substance, and (ii) a pharmaceutically acceptable carrier for releasing the substance over time to prevent restenosis.

29. A method as defined in claim 28, wherein the pharmaceutically acceptable carrier is non-solid.

30. A method as defined in claim 28, wherein the pharmaceutically acceptable carrier comprises a polymer.

31. A method as defined in claim 28, wherein the blood vessel or graft has suffered a vascular injury.

32. A method as defined in claim 28, further comprising the step of delivering a second composition to substantially the same location as the first composition.

33. A method as defined as claim 32, wherein the second composition is non-solid and comprises a cross-linker.

34. A method as defined in claim 28, wherein said delivering step comprises percutaneously injecting the composition through a curved tubular member.

35. A method as defined in claim 34, wherein said composition is nonintramurally delivered relative to said blood vessel or graft.

36. A method for percutaneously administering localized delivery of a biologically active substance to a desired location in vivo comprising the steps of:

a) selecting an internal locus for treatment; and b) delivering to the selected locus a first composition comprising (i) a biologically active substance, and (ii) a pharmaceutically acceptable non-solid carrier for releasing the substance over a period of time.

37. A method as defined in claim 36, wherein the pharmaceutically acceptable non-solid carrier comprises a polymer.

38. A method as defined in claim 37 further comprising the step of administering a second composition to substantially the same location as the first composition.

39. A method as defined in claim 38, wherein the second composition comprises a cross-linker.

40. A method as defined in claim 37, wherein the polymer comprises a polysaccharide.

41. A method as defined in claim 40, wherein the polysaccharide comprises alginate.

42. A method as defined in claim 36, wherein the first composition comprises at least one biologically active substance which is selected from the group consisting of a gene, a gene regulator, an antibody, a polypeptide, a radioactive composition, a drug or any combination thereof.

43. A method as defined in claim 36, wherein the delivering step comprises injecting through a curved tubular member.

44. A method for treating a blood vessel or graft comprising the steps of:

a) selecting a blood vessel or graft for which treatment is desired; and b) delivering to a periadventitial area of the blood vessel or graft in vivo a first composition comprising (i) a biologically active substance, and (ii) a pharmaceutically acceptable carrier for releasing the substance over time to treat the blood vessel or graft.

45. A method as defined in claim 44, wherein the pharmaceutically acceptable carrier comprises a polymer.

46. A method as defined in claim 44, further comprising the step of delivering a second composition to substantially the same location as the first composition.

47. A method as defined in claim 46, wherein the second composition is non-solid and comprises a cross-linker.

48. A method as defined in claim 44, wherein the first composition comprises at least one biologically active substance which is selected from the group consisting of a gene, a gene regulator, an antibody, a polypeptide, a radioactive composition, a drug, or any combination thereof.

49. A method as defined in claim 44, wherein said delivering step comprises percutaneously injecting the composition through a tubular member.

50. A method as defined in claim 49, wherein said tubular member is curved.

51. A method as defined in claim 50, wherein the curved tubular member comprises a lumen opening and a piercing portion and wherein said injecting through a curved tubular member comprises the steps of:

a) advancing the curved tubular member around a first side of the locus to be treated to a first location substantially overlying the locus, the tubular member being capable of delivering a first non-solid composition; and b) injecting the first non-solid composition through the lumen opening as the piercing part is withdrawn from the first location to a second location.

52. A method as defined in claim 51, further comprising the steps of:

c) turning the tubular member about 180°;

d) advancing the tubular member such that the piercing part of the tubular member moves around a second side of the locus to a third location substantially near the first location; and e) injecting the first non-solid composition through the lumen opening as the piercing part is withdrawn from the third location to a fourth location substantially the same as the second location.

53. A method as defined in claim 51, further comprising the step of injecting a second non-solid composition into substantially the same locations as the first non-solid composition.

54. A method as defined in claim 53, wherein the tubular member comprises at least two lumens and wherein the first and second compositions are injected substantially simultaneously therefrom.

55. A method for treating a blood vessel or graft comprising the steps of:

a) selecting a blood vessel or graft for which treatment is desired; and b) nonintramurally delivering to a periadventitial area of the blood vessel or graft in vivo a first composition comprising (i) a biologically active substance, and (ii) a pharmaceutically acceptable non-solid carrier for releasing the substance over time to treat the blood vessel or graft.

56. A method as defined in claim 55, further comprising the step of delivering a second composition to substantially the same location as the first composition.

57. A method as defined in claim 56, wherein the second composition comprises a cross-linker.

58. A method as defined in claim 55, wherein said delivering step comprises percutaneously injecting through a tubular member.

59. A method as defined in claim 58, wherein said tubular member is curved.

* * * * *